Oct. 14, 1958 E. S. BOERNER Plant Pat. 1,764
ROSE PLANT
Filed March 5, 1958
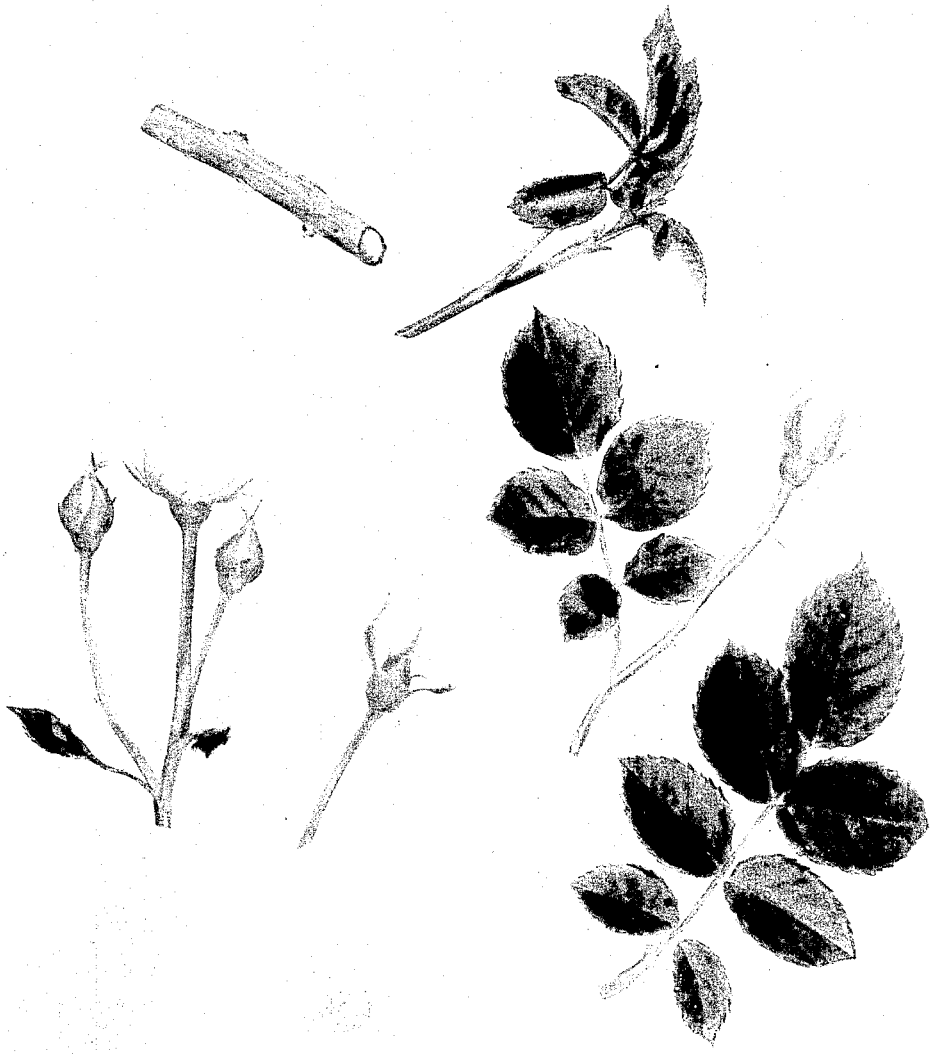
Inventor.
E. S. Boerner
By: Robb & Robb
Attorneys.

United States Patent Office

Plant Pat. 1,764
Patented Oct. 14, 1958

1,764

ROSE PLANT

Eugene S. Boerner, Newark, N. Y., assignor to Jackson & Perkins Company, Newark, N. Y., a corporation of New York Application March 5, 1958, Serial No. 719,464

1 Claim. (Cl. 47—61)

The present invention relates to a new and distinct variety of rose plant of the large-flowered polyantha class, which was originated by me by crossing the variety "Goldilocks" (Plant Patent No. 672) with the variety "Pigmy Gold" (Plant Patent No. 1,114).

The primary objective of this breeding was to produce a new rose variety of the yellow floribunda type which has full and compact habits of growth so as to make it better suited for use by florists as a pot forcing variety. This objective was fully achieved, along with other improvements, as evidenced by the following unique combination of characteristics which are outstanding in the new variety and distinguish it from its parents, as well as from all other varieties of which I am aware:

(1) Compact, full and upright habits of growth;

(2) Very dark young foliage, corresponding in general color tonality to Victoria Lake, which is unusual in a yellow-flowered floribunda;

(3) Free production of long-lasting flowers; and (4) Empire Yellow general color tonality of the flowers in all stages of bloom.

Asexual reproduction of the new variety by budding, as performed at Newark, New York, and also at Pleasanton, California, shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with Ridgway's Color Standards and Nomenclature:

Parentage: Seedling.
- *Seed parent.*—"Goldilocks."
- *Pollen parent.*—"Pigmy Gold."

Classification:
- *Botanic.*—Large-flowered polyantha.
- *Commercial.*—Floribunda.

*Flower*

(Observations made from specimens grown in a greenhouse at Newark, New York, in the early morning in the early part of May.)

Blooming habit: Recurrent—continuous.

Bud:
- *Size.*—Medium.
- *Form.*—Ovoid; is not affected by wet or hot weather.
- *Color.*—When sepals first divide—Deep Chrome, Plate 3. When petals begin to unfurl—Light Orange-Yellow, Plate 3 lightly overcast with Deep Chrome, Plate 3. When half-blown: inside of petals—Light Cadmium, Plate 4, with outer edges lightly overcast with Maize Yellow, Plate 4; reverse of petals—Light Orange-Yellow, Plate 3, lightly overcast with Deep Chrome, Plate 3.

- *Sepals.*—Branched; curl back when petals begin to unfurl. Color: inside—Chrysolite Green, Plate 31; outside—Light Bice Green, Plate 17.
- *Calyx.*—Color—Lettuce Green, Plate 5. Shape—funnel. Size—small. Aspect—smooth. Odor when rubbed—none.
- *Peduncle.*—Length — medium. Strength — erect; heavy. Aspect—smooth. Color—Lettuce Green, Plate 5.
- *Opening.*—Opens up well; is not affected by adverse weather conditions.

Bloom:
- *Size.*—Large. Average size when fully expanded—4 inches.
- *Borne.*—Both singly and several together.
- *Stem.*—Medium length; strong.
- *Form (when first open).*—Full. Permanence—retains its form to the end, but outer petals curl back.
- *Petalage.*—Double (full but open center). Number of petals under normal conditions—from 25 to 30.
- *Color.*—Center of flower—Deep Chrome, Plate 4. Outer petals—Pinard Yellow, Plate 4, with outer edges of petals lightly overcast with Empire Yellow, Plate 4. Base of petals (aiglet)—Lemon Yellow, Plate 4. Inside of petals—Empire Yellow, Plate 4. Reverse of petals.—Amber Yellow, Plate 16. General tonality from a distance—Deep Chrome, Plate 4.
- *Discoloration.*—General tonality at end of first day—Empire Yellow, Plate 4, with outer edges of petals lightly overcast with Deep Chrome, Plate 4. Second day—Empire Yellow, Plate 4, with outer edges of petals lightly overcast with Deep Chrome, Plate 4. Third day—Empire Yellow, Plate 4.

Petals:
- *Texture.*—Leathery; is not affected by wet or hot weather.
- *Appearance.*—Inside—satiny. Outside—shiny.
- *Form.*—Oval; slightly notched.
- *Arrangement.*—Imbricated (regularly arranged shingle-like).
- *Petaloids in center.*—Few; large.
- *Persistence.*—Drop off cleanly.
- *Fragrance.*—Moderate. Nature—tea (average hybrid tea scent).
- *Lasting quality.*—On the plant—very long. As cut flower—very long.

*Genital organs*

Stamens, Anthers: Medium size; many; regularly arranged around styles. Color—Capucine Yellow, Plate 3.

Stamens, filaments (threads): Medium length. Color—Empire Yellow, Plate 4, with lower half of filament Spectrum Red, Plate 1.

Pollen: Color—Maize Yellow, Plate 4.

Styles: Loosely separated; uneven length; medium length; thin.

Stigmas: Color—Pinard Yellow, Plate 4.

Ovaries: Some protruding from calyx.

Hips: None.

Seeds: None.

*Plant*

Form: Bush.

Growth: Vigorous; upright; busy; compact.

Foliage: Compound of 5 to 7 leaflets.
- *Size.*—Medium.
- *Quantity.*—Abundant.
- *Color.*—New foliage: upper side—Victoria Lake, Plate 1; under side—Garnet Brown, Plate 1. Old foliage: upper side—Forest Green, Plate 17; under side—Light Elm Green, Plate 17.

*Shape.*—Oval pointed.

*Texture.*—Upper side—leathery. Under side—smooth.

*Ribs and veins.*—Ordinary.

*Edge.*—Serrated (saw-toothed).

*Serration.*—Both double and single; sharp.

*Leaf stem.*—Color—Light Bice Green, Plate 17. Under side—prickly.

*Stipules.*—Medium length; bearded.

Wood:

*New wood.*—Color—Spinach Green, Plate 5. Bark—smooth.

*Old wood.*—Color—Light Bice Green, Plate 17. Bark—smooth.

Thorns:

*Thorns.*—Quantity: on main stalks from base— many; on laterals from stalk—many. Form—flat base; long; straight. Color (when young)—Chartreuse Yellow, Plate 31. Position—irregular.

*Prickles.*—Quantity: on main stalks—none; on laterals—none.

*Short needles.*—Quantity: on main stalks—none; on laterals—none.

I claim:

A new and distinct variety of rose plant of the large-flowered polyantha class, substantially as herein shown and described, characterized particularly as to novelty by the unique combination of compact, full and upright habits of growth, very dark colored young foliage corresponding to Victoria Lake in general color tonality, free production of long-lasting flowers, and the Empire Yellow general color tonality of the flowers in all stages of bloom.

No references cited.